(12) United States Patent  
Eid et al.

(10) Patent No.: US 8,465,922 B2
(45) Date of Patent: Jun. 18, 2013

(54) METHODS AND SYSTEMS FOR MONITORING REACTIONS

(75) Inventors: John Eid, San Francisco, CA (US); Stephen Turner, Menlo Park, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 0 days.

(21) Appl. No.: 13/217,112

(22) Filed: Aug. 24, 2011

(65) Prior Publication Data

US 2012/0052490 A1  Mar. 1, 2012

Related U.S. Application Data

(60) Provisional application No. 61/377,396, filed on Aug. 26, 2010.

(51) Int. Cl.
| C12Q 1/68 | (2006.01) |
| C12P 19/34 | (2006.01) |
| C07H 21/04 | (2006.01) |
| G01N 21/00 | (2006.01) |

(52) U.S. Cl.
USPC ....... 435/6.1; 435/6.12; 435/91.2; 435/287.2; 536/23.1; 536/24.33; 422/82.05

(58) Field of Classification Search
None
See application file for complete search history.

(56) References Cited

U.S. PATENT DOCUMENTS

| 5,547,839 A | 8/1996 | Dower et al. |
| 6,210,896 B1 | 4/2001 | Chan |
| 6,255,083 B1 | 7/2001 | Williams |
| 6,787,308 B2 | 9/2004 | Balasubramanian et al. |
| 6,917,726 B2 | 7/2005 | Levene et al. |
| 7,056,661 B2 | 6/2006 | Korlach et al. |
| 7,170,050 B2 | 1/2007 | Turner et al. |
| 8,182,993 B2 * | 5/2012 | Tomaney et al. ............ 435/6.12 |
| 2002/0106649 A1 * | 8/2002 | Lizardi et al. ..................... 435/6 |
| 2003/0096253 A1 | 5/2003 | Nelson et al. |
| 2003/0190647 A1 | 10/2003 | Odera |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2009/0024331 A1 | 1/2009 | Tomaney et al. |
| 2011/0065607 A1 * | 3/2011 | Kersey et al. ................... 506/16 |

FOREIGN PATENT DOCUMENTS

| WO | 9106678 A1 | 5/1991 |
| WO | 9627025 A1 | 9/1996 |
| WO | 9905315 A2 | 2/1999 |
| WO | WO2007/123744 | * 11/2007 |

OTHER PUBLICATIONS

Eid, et al., "Real-time DNA sequencing from single polymerase molecules" Science (2009) 323(5910):133-138.
Levene et al., "Zero-mode waveguides for single-molecule analysis at high concentrations" Science (2003) 299(5807):682-686.

* cited by examiner

*Primary Examiner* — Betty Forman
(74) *Attorney, Agent, or Firm* — Robert H. Reamey

(57) ABSTRACT

Methods and systems for monitoring reactions by observing signals deriving from those reactions, using signal processing that allows differentiation between signals that are otherwise optically overlapping by conventional detection methods. Centroid determination is used to identify signal sources that are presenting confounding overlapping signals due to their physical proximity, and/or to identify discrete signals from different reaction centers.

11 Claims, 4 Drawing Sheets

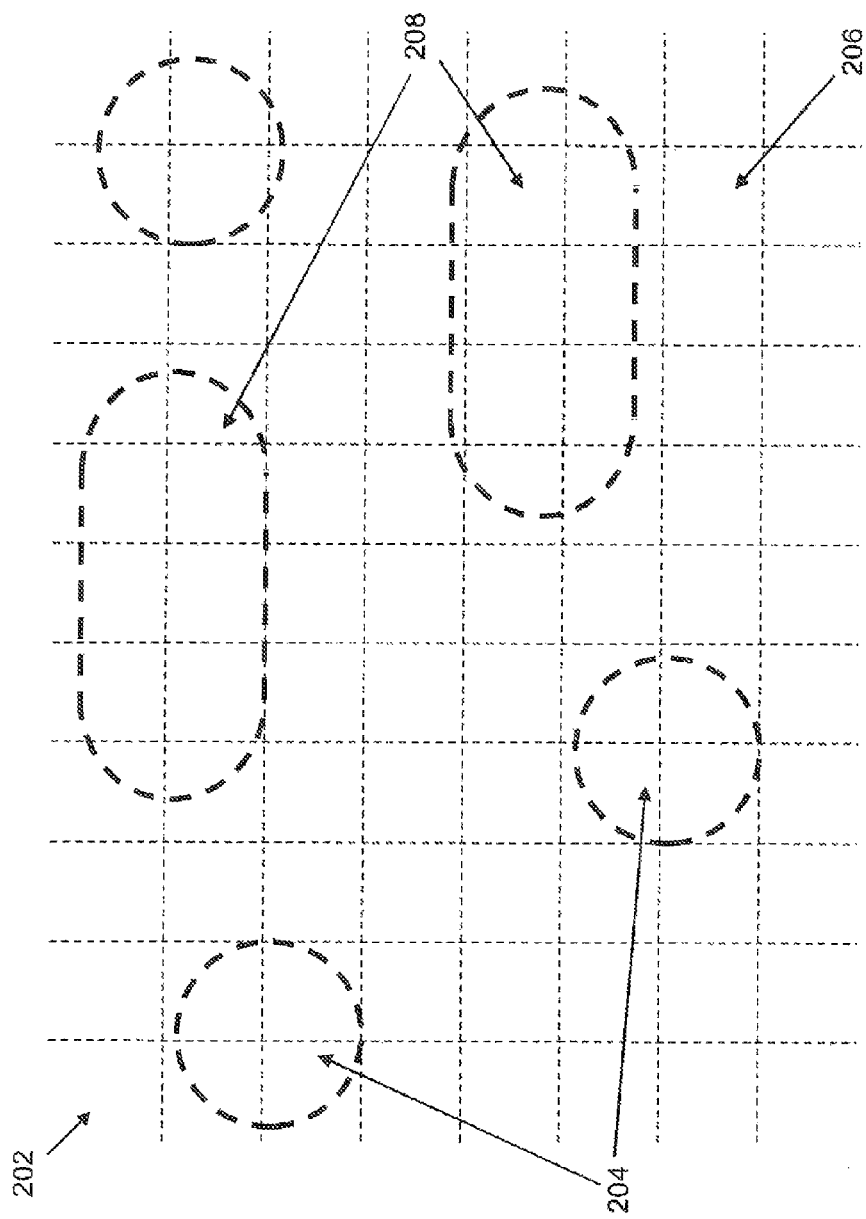

METHODS AND SYSTEMS FOR MONITORING REACTIONS

CROSS-REFERENCE TO RELATED APPLICATIONS

This application claims the benefit of Provisional U.S. Patent Application No. 61/377,396, filed Aug. 26, 2010, the full disclosure of which is incorporated herein by reference in its entirety for all purposes.

STATEMENT REGARDING FEDERALLY SPONSORED RESEARCH

Not Applicable.

BACKGROUND OF THE INVENTION

Advances in bioanalytical technologies have provided greater and greater amounts of information on the operation of biological processes, how different processes operate together, and how one might influence those processes through the application of external pressures, e.g., through the introduction of outside agents like pharmaceutical compounds, changes in environments, etc. Typically, such analyses rely on the observation of certain highly biologically relevant reactions and processes to monitor their progress, rate, and one's ability to influence them. In some cases, the reactions are employed as tools for identifying the characteristics of other components of the reaction, based upon how the reaction progresses. For example, nucleic acid synthesis reactions have been monitored in order to identify the sequence of the template nucleic acid against which the product is synthesized, by identifying the nucleotides incorporated at each position in that sequence.

In general, these relevant reactions are monitored by looking at populations or ensembles of molecules all reacting together, to provide a monitorable reaction product. These reaction populations or ensembles are typically provided in homogeneous patches or regions on substrates, or in wells of a multiwall substrate.

Such ensemble approaches provide a number of useful properties, including signal availability from larger collections of reactions, averaging of individual molecular reaction variations over the ensemble, and ease of use with conventional measuring tools, e.g., fluidic measurements, optical measurements, or the like. However, some of these traits, while advantageous in one context, are detrimental in others. For example, where ensemble approaches average over the entire population of reactions, one is, as a result, unable to see potentially important events at the individual reaction level. Similarly, by watching only an ensemble reaction, one is often required to artificially start and stop reactions to identify specific events, e.g., through the use of terminating reactants, by limiting necessary reactants, or the like.

For a number of applications, the ability to monitor individual reaction complexes, or single molecule reactions, provides the ability to directly observe a given reaction, as well as those influences upon that reaction. For example, the ability to directly, and in real time, detect the incorporation and identity of nucleotide building blocks into the template directed synthesis of nucleic acids, e.g., DNA and RNA, provides the ability to, by implication, derive the underlying sequence of the particular nucleic acid template. Because individual molecules are being observed, one can continuously observe the synthesis reaction, and thus 'read out' extremely long segments of the underlying template sequence.

Systems have been developed that are capable of directly monitoring individual reaction complexes in real time. One such system is the SMRT Sequencing system that employs optically confined reaction volumes coupled to highly sensitive multiplexed fluorescent illumination and detection systems. The result is illumination of very small volumes immediately surrounding an individual immobilized reaction complex in order to excite fluorescent reagents as they are taking part in the reaction of interest. The fluorescent signals are then transmitted in parallel through optical trains to separate signals having different spectral characteristics, e.g., resulting from different reactions, to be directed at sensitive sensor arrays. The position on the sensor array operates to identify the specific reaction that yielded a given signal.

In order to improve the throughput of these systems, one must increase the number of individual reactions that are observed at any given time. Because these reaction complexes are immobilized, this typically involves one or both of increasing the observed area containing the immobilized complexes and/or increasing the density of reaction complexes in a given area. With respect to the latter approach, one often encounters limitations of how densely reaction complexes can be packed on a surface, and still resolve adjacent reactions from each other. In particular, depending upon the nature of the optical system, and the detector used, e.g., the pixel size and count, signals from adjacent reaction complexes, where too closely packed, will be detected as a single unified or otherwise unparsable signal, or will otherwise overlap with each other, such that simple discrimination between two signals becomes more difficult.

The present invention, on the other hand, provides methods systems, and consequently, reaction substrates, that provide the ability to have more densely packed reaction complexes while still permitting the resolution of otherwise unresolvable signals. Further, these same methods are applicable for other applications, including identification and discrimination of individual or multi-reaction signals, and the like.

BRIEF SUMMARY OF THE INVENTION

The invention is directed to the deconvolution of imaged signal data arising from multiple optically interrogated reaction centers on a particular medium, substrate or the like, where the imaged signals overlap positionally, and in some cases, temporally; on an imaging detector. In particular, the present invention employs centroid identification to identify overlapping signals that potentially arise from more than one reaction center, and either employ that identification to filter out overlapping data or interpret such overlapping data.

BRIEF DESCRIPTION OF THE DRAWINGS

FIG. 2 illustrates overlapping signal events imaged upon a sensor.

DETAILED DESCRIPTION OF THE INVENTION

I. Single Molecule Detection

A. Generally

Figure 1:
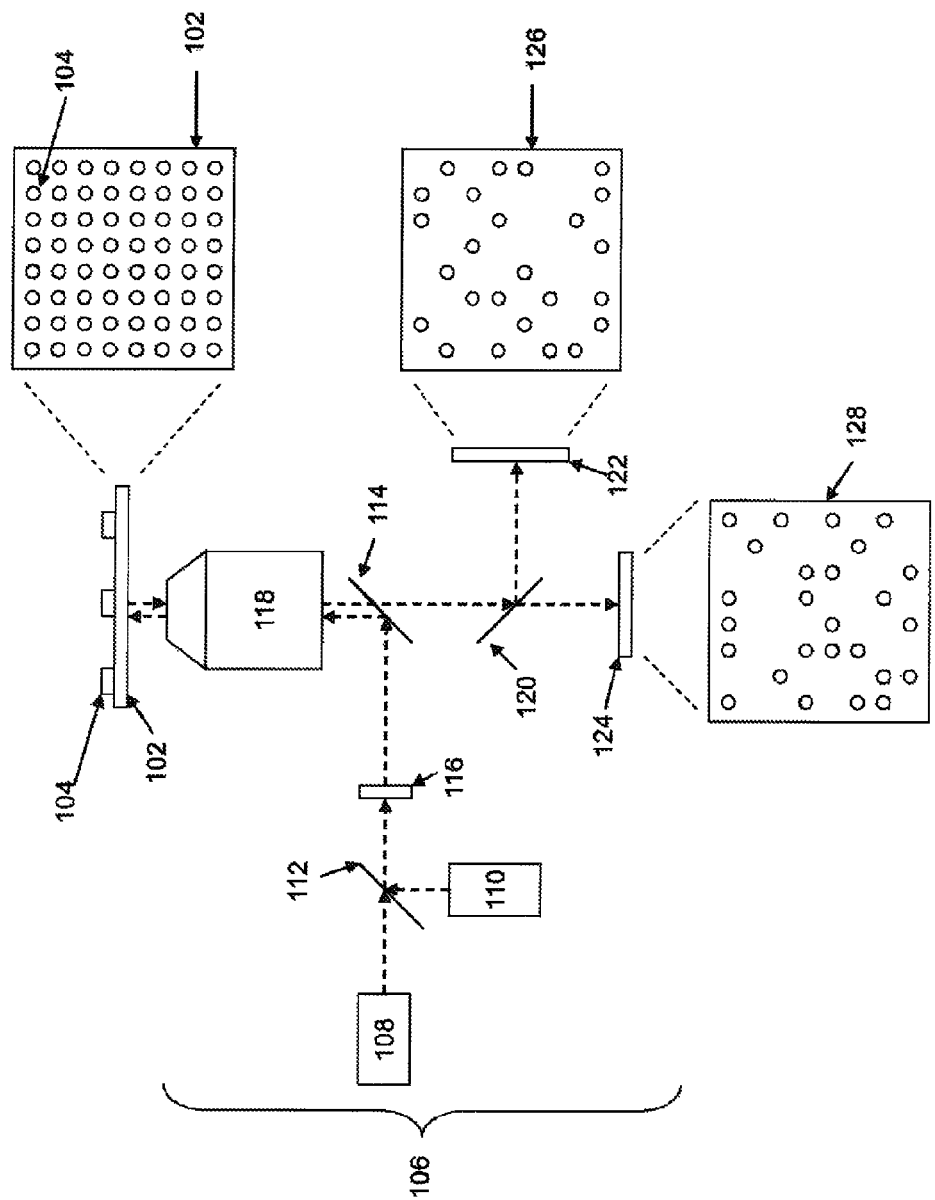
FIG. 1 provides a schematic illustration of an overall system for performing analytical reactions.

As noted above, the monitoring of individual reaction complexes, also referred to herein as single molecule reactions, typically involves observing a reaction complex that produces a detectable signal that is indicative of the reaction of interest. Such signals may include optically detectable signals, electrochemically detectable signals, thermal signals, mass based signals, or the like.

In particularly preferred aspects, optically detectable signals are used to monitor the reactions of interest. Through the use of labeling groups that have high quantum yields, one can provide a relatively large signal from a single molecule of reagent. Examples of such groups include, for example any of a variety of fluorescent organic dyes, such as fluorescein or cyanine based dyes. A large number of such dyes are known in the art and are generally available from a number of commercial sources, including, e.g., Cy 3 and Cy5 families of dyes from GE Healthcare (Piscataway, N.J.), and the AlexaFluor® dyes available from Life Technologies (Carlsbad, Calif.). Other high quantum yield labels include semiconductor nanocrystals, also available from Life Technologies and eBiosciences (San Diego, Calif.).

In the context of optically detectable species, it will be appreciated that the reaction of interest may produce an optically detectable component, e.g., a direct or indirect fluorescent signal, or it may produce a shift in one or more optical characteristics of the detectable component, e.g., change in fluorescent absorption and/or emission spectra, shift in rotational diffusion rate, or shift in fluorescence lifetime. In further aspects, the reaction of interest may result in the entrainment, immobilization or retention of the optically detectable species within a defined space for a longer period than would result from random diffusion. Such immobilization based methods include the incorporation of the detectable species within the reaction product, but can also include the retention of the optically detectable component in the reaction complex for an observably longer period of time.

For single molecule reactions, detection of optically detectable signals typically relies upon immobilization of the individual reaction complexes such that the signals may be observed and identified as deriving from a given reaction complex. Such immobilization may include immobilization at a set location upon a substrate, such that multiple reaction complexes are arrayed over the surface for multiplexed analysis. Alternatively, such reaction complexes may be provided upon other solid supports, like beads or other particles, such that the complexes may be fluidly transported as necessary for logistic reasons, or for other benefits. Detection of the reactions of interest, and particularly those relying upon the monitoring of fluorescent signals, typically provide for the illumination of the reaction complex with an excitation light source that provides light of a sufficient excitation wavelength for excitation of the fluorescence within the given fluorescent group or groups, which thereupon results in generation of a fluorescent signal. Such signal may be a direct fluorescent emission, in response to excitation by the excitation light source, or it may be an indirect fluorescent signal that results from the energy transfer from a donor fluorophore which was, itself, excited by the excitation light source.

The fluorescent signals generally are then conveyed through an appropriate optical train to a detector, as described in greater detail below, which detects the optical signal, and in many cases, does so in a manner that also conveys information about the location upon the substrate from which the signal emanated.

In alternative aspects, electrochemically detectable signals may also be employed. Such signals typically derive from changes in the electrical charge in one or more of the reagents for the reaction, or within the environment surrounding the reaction of interest. By way of example, reactions that result in the addition or removal of highly charged groups may be detectable based upon the change in charge. While such detection may be accomplished through a variety of different mechanisms, e.g., through identifying changes in the electrokinetic mobility of the reagents, through the ability of the reagents to associate with counter-charged species, or the like, for single molecule reactions, such methods are not preferred. Instead, more sensitive detection mechanisms that directly detect changes in the localized charge are preferred. Such systems include, for example, micro-electrochemical sensors, such as ChemFETs and nano-ChemFETs, that detect localized shifts in charge from a reaction complex coupled to the sensor, as a field effect that gates an underlying transistor channel element. Other electrochemical sensors detect shifts in the protonation level or pH of the local environment, which shifts result from the reaction of interest.

The detected signals may result from the initiation, progress or completion of the reaction of interest or from an event that precedes or succeeds the reaction of interest, e.g., as an upstream or downstream reaction, respectively. In particular, and as alluded to above, the signal may be detected that results from incorporation of a labeled component into the reaction product. As a result, the detection will typically occur after the occurrence of the reaction of interest. Examples of such reactions include, e.g., synthetic reactions, such as nucleic acid synthesis reactions, where fluorescently labeled nucleotides are incorporated into a nascent nucleic acid sequence, and by virtue of a label component provided on a retained component of the nucleotide, e.g., a base or sugar portion, result in the incorporation of the label. One can identify the incorporation by identifying the presence of the fluorescent label in the reaction product. Other reaction products are monitored through the release of a quenched fluorescent molecule, resulting in a de-quenching and resulting fluorescent signal.

Still other reactions are monitored by detecting the initiation or progress of the reaction. For example, in another nucleic acid synthesis reaction, the presence of a fluorescently labeled nucleotide at or near the active site of a polymerase enzyme can be observed by virtue of its location. In one aspect, a cooperative labeling component is provided at or near the active site of the polymerase which interacts with the label component on the nucleotide to yield the fluorescent signal upon interaction of the acceptor fluorophore on the nucleotide with a donor fluorophore at or near the active site of the polymerase (See, e.g., U.S. Pat. No. 7,416,844, the full disclosure of which is incorporated herein by reference in its entirety for all purposes). In another aspect, the polymerase enzyme is provided under confined illumination, i.e., within an illumination volume that encompasses the enzyme and its active site, but not a much greater volume. Retention of the fluorescent reagent within that volume in conjunction with the reaction of interest is then detectable over and above the random diffusion of fluorescent molecules into and out of that volume (See, e.g., U.S. Pat. No. 7,485,424, the full disclosure of which is hereby incorporated herein by reference in its entirety for all purposes).

B. Identification of Individual Reactions

As noted above, in many single molecule and ensemble reaction analytical systems, the reaction complexes are provided immobilized in fixed locations upon substrates or other solid supports. Typically, higher throughput for such systems is gained by providing multiple reaction complexes or multiple reaction sites within a given area on the substrate. In order to be able to accurately identify signals from a given reaction complex or reaction site, the multiple complexes or sites are typically provided upon the surface in an optically resolvable spacing. Rephrased, different reaction complexes or reaction sites are positioned that they may be readily identified as a given reaction complex or site based upon the spatial or localization characteristics of the reaction (or signals emanating therefrom). This typically entails depositing the complexes or reaction sites upon the surface at a density that allows for individual optical resolution of such individual reaction complexes or sites. Stated another way, optical resolution of adjacent reaction complexes typically means that the complexes have to be sufficiently far apart that there is little or no signal overlap at the detection point in the system, such that signal contribution from individual reactions can be unambiguously identified.

In the context of conventional microscopy, this typically requires that adjacent reaction complexes or sites be a distance of at least $\lambda/(2NA)$, where $\lambda$ is the wavelength of the light being collected from the reaction complex and NA is the numerical aperture of the microscope, apart on the substrate, such that the resulting signals imaged at the detector are spaced sufficiently far apart to meet the Rayleigh criterion for the minimum resolvable detail. For array based detectors, there is the added element of ensuring that such spacing is evident at the pixel level, as pixilation can impact the optical resolution beyond the Rayleigh diffraction limit, i.e., there is a general need to ensure that there is at least one pixel of space between the signals at the detector. This permits an unambiguous determination that a given detected signal derives from an individual reaction region. In the context of the present invention, a given reaction event, whether that be of an individual reaction complex at a single molecular or complex level, or an ensemble reaction event that is based upon multiple molecules or complexes of the same make up, is generally referred to as a reaction center. Thus, a reaction center may include an individual molecular complex, i.e., in a single molecule analysis, or it may include a collection of identical molecules or complexes, that are separate from other collections of different molecules or complexes. In particularly preferred aspects, reaction centers include single molecules or molecular complexes.

Typically, spacing of individual reaction complexes has been addressed through a number of mechanisms, including, for example, application of diluted surface modifiers (See, e.g., U.S. Pat. No. 7,763,423, the full disclosure of which is hereby incorporated herein by reference in its entirety for all purposes) to yield a low density reactive surface that results in the ability to couple reaction complexes, probabalistically speaking, at an optically resolvable density. Other alternative or complementary mechanisms employ biased immobilization schemes that selectively activate portions of the surface of the underlying substrate, so as to increase the likelihood that immobilized complexes are provided at desired locations and at optically resolvable densities (See, Published U.S. Patent Application Nos. 2008-0032301). Still other approaches employ structural barriers or divisions between adjacent reaction regions, that may be used alone or in conjunction with other approaches described herein, to provide sufficient spacing between reaction complexes or sites.

Despite their effectiveness at providing optically resolvable complexes, in many cases, such approaches rely upon the Poisson distribution of complexes on a surface. As such, there is some level of probability that adjacent complexes will not be sufficiently spaced to be optically resolvable. Further, as one desires to increase the throughput of a given system, it would be highly beneficial to increase the density of observed complexes in a unit area of analytical substrate. As will be appreciated, however, such an increase in density carries with it a concurrent loss in individual optical resolution as the probability of adjacent complexes being optically unresolvable increases. The use of substrates having such immobilized complexes is better understood in the context of an exemplary detection and analysis system.

FIG. 1 schematically illustrates one example system for monitoring reactions that are provided in different locations on a reaction substrate. As shown, a reaction substrate 102 is provided that includes multiple discrete reaction sites 104 disposed upon its surface. These reaction sites may be randomly dispersed across the surface, or they may be selectively arrayed over the surface in preselected locations or patterns, e.g., gridded arrays, or the like. As shown the substrate 102 is provided in optical communication with a fluorescence detection system 106, that includes one or more excitation light sources, such as lasers 108 and 110, and an optical train the directs excitation light from the excitation source to the substrate to excite fluorescent signals in the various reaction regions 102. As shown, the optical train includes one or more dichroics, e.g., dichroic 112 and 114, to co-direct one or more excitation wavelengths to the reaction regions 102. Also shown is an additional optional optical element, e.g., a diffractive optical element 116, which configures the excitation beam to provide targeted illumination of multiple discrete reaction regions, by splitting individual excitation beams in to large numbers of discrete beamlets. The beamlets are then directed through an objective lens 118 or lens assembly, to direct and focus the excitation beam or beamlets onto the substrate at the reaction regions 104. A number of other optical elements are also typically included within the optical train depending upon the nature of the application, such as additional lenses, filters, and the like, but are not shown, in order to facilitate basic description of the system.

Fluorescent signals arising from reactions at the reaction regions under excitation illumination, are collected by the objective lens 118, and passed through dichroic 114 into a separate part of the optical train that directs these fluorescent signals to one or more imaging detectors or sensor arrays. As shown, the signals are directed to an additional dichroic 120, that selectively reflects or passes signal components that have different spectral characteristics, arising from, e.g., the use of different fluorescent labeling groups. For example, as noted elsewhere herein, different reagents may include spectrally different label groups whose signals will be differentially reflected or passed by dichroic 120. The differing signals are then directed to and imaged upon different detectors, e.g., detectors 122 and 124, yielding signal images 126 and 128, respectively, on those detectors. Optionally, the signals may be passed through a dispersive optical element which differentially directs spectrally different signals or signal components and images those signals or signal components onto different locations on the same detector (See, e.g., Published U.S. Patent Application No. 2007-019582). Again, additional optical elements may be included in the optical train that directs these signals to the detector, such as imaging lenses, filters, e.g., confocal filters or filter masks, and the like.

Spatially distinct reaction regions will optimally be directed to and/or imaged upon different portions of the detector. As noted previously, in ideal circumstances, such imaged signals will be optically resolvable from each other. However, in many cases, signals from adjacent reaction regions, e.g., individual molecular complexes, may overlap to produce potentially confounding signal events.

II. Individual Signal Characteristic

The present invention is directed to the detection from and attribution of signals to individual reaction complexes or reaction sites that are disposed upon a substrate in a manner that does not require complete spatial separation of such sites or complexes so as to yield otherwise complete optical resolution. In particular, the present invention utilizes characteristics of individual signal events (whether from a single molecule or complex reaction, or from a single region of reactants used in an ensemble reaction approach). By using characteristics that do not require complete spatial separation of adjacent regions, one can both increase the density of reaction regions in a given area, and resolve signals from regions that would otherwise have been lost as not resolvable. Through both benefits, one can increase the throughput of the system by deriving usable data from more reaction regions. Similarly, one can improve the overall accuracy of the system by eliminating or reducing confounded signals from regions that are spatially close together.

In certain aspects, the individual signal characteristic is a spatial characteristic, such as a signal centroid, while in other aspects, other signal characteristics are exploited, such as spectral characteristics, interactive characteristics, temporal characteristics, and the like. In still other aspects, both spatial and other signal characteristics are employed in combination to assign a signal event to a given reaction complex or site.

Under the above-described approaches, a signal characteristic that is assignable to an individual signal, as opposed to a confounded signal is used to resolve the particular signal event, and/or resolve subsequent signal events from that same location on a substrate, without reliance upon such signals emanating from completely separate and optically resolvable locations.

A. Centroid Based Discrimination

In accordance with the present invention, molecular complexes that are not otherwise optically resolvable, as set forth above, may nonetheless be observed and used to provide meaningful and identifiable signal data. In particular, as shown in FIG. 1, the simplified schematic of an analytical system is provided. The system 100 includes an analytical substrate 102 that includes a plurality of individual reaction regions 104 that include molecular reaction region disposed upon its surface, and preferably immobilized as shown.

FIG. 2 schematically illustrates imaged signals from reaction complexes on the detector array that is made up of multiple pixel elements. As shown, FIG. 2 shows the image of a signals 204 that results from an individual complex, on a detector array 202 having multiple pixel elements (e.g., pixel element 206) as well as the images resulting from signals 208 arising from adjacent complexes, where the imaged signals overlap, e.g., on common pixel elements, and would not be generally considered to be optically resolvable, as set forth above. Typically, where a signal results from the aggregation of signals from reaction centers that are not optically resolvable, the data deriving from that signal image provides confused data, e.g., mixed data from multiple different reactions. In particular, where the signal detected at a given location results from two overlapping reaction centers, each operating independently of the other, the resulting data derived from that image can be confusing, much like listening to two different conversations being carried out simultaneously.

Because of this confusion, the use of such signals will reduce the level of integrity associated with the overall system by yielding some expected fraction of inaccurate data, or in excessive filtering of all data such that only data that is unimpeachable in its accuracy is used. In either of these cases, the overall throughput of the system is reduced.

In a broad aspect, the present invention provides the ability to identify multi-reaction signals (resulting from multiple reaction centers) that otherwise are imaged as a single contiguous signal, and either characterize such signals as multi-reaction, so that such signals may be discarded or otherwise treated differently from single reaction signals, or further process such signals to derive useful information despite the presence of multiple reactions in a single contiguous image. The invention achieves this, in a general sense, by analyzing the signal characteristics of a given signal image and determining whether such characteristics are indicative of one or more reaction centers producing such signals. Such determination may utilize the comparison of the signal of interest with known signal characteristics of single, double and other multiple reaction center signals. Additionally or alternatively, the determination may evaluate signal information, de novo, to identify specific characteristics that are indicative of individual or multiple reaction signals.

In one aspect, the present invention characterizes the individual signals by identifying the signal centroids based upon the image of the centroid on the detector, e.g., a CCD, iCCD, EMCCD, or CMOS sensor array. Where multiple centroids are determined for an individual signal image component, it will be identified as corresponding to multiple reaction centers.

Identification of centroids may generally be accomplished using a number of known signal processing methods. For example, in one aspect, the invention utilizes a point spread function for the imaged signal to identify the center point or centroid of a given imaged signal. Further, this process permits the centroid identification at the sub-pixel level or with greater than 1 pixel sensitivity on the sensor array. Previously, the use of such centroids have been exploited for aiding the identification of separated spectral components of a given reaction signal (See, e.g., U.S. Patent Application No. 2009-0024331). In particular, in a reaction that produces spectrally different optical signals based upon the nature of the reaction taking place, one would subject the signal to a spectral separation process that would differently image the spectrally different signals onto the detector array. Given less than complete spectral separation of signal components at the image plane that resulted from an individual reaction complex, one could nonetheless identify a distinct spectral signal through identification of the centroid of the spatially separated image of the spectral components on the detector. By identifying the spectral centroid, one could then identify the spectral characteristics of the given signal, and thus identify or characterize the reaction that produced the signal.

In contrast, the present invention utilizes centroid determination, optionally at the subpixel level, to identify signals that result from multiple reaction centers that are otherwise optically unresolvable and/or to interpret signal data from such optically unresolvable signals. In particular, by identifying signal events that have different centroids, despite having the same spectral characteristics, one can identify such signals as emanating from different reaction centers. Further, one can then use such centroids to assign subsequent signals to each of the different reaction centers based upon its own unique centroid.

III. Application of Centroid Information

The identification of centroids for individual reaction centers that are otherwise unresolvable can impart a number of advantages. For example, as noted previously, such methods can be employed to identify reaction centers that are multiply occupied, and thus susceptible to lower monitoring accuracy (due to potentially confounding signals), or they can serve to identify and assign signal components to optically contiguous but otherwise discrete reaction centers, such that one may derive useful data from such optically contiguous reaction centers. Other advantages would also be apparent to the skilled artisan.

For purposes of illustration, the methods of the invention are described with reference to a single molecule nucleic acid sequencing process, where individual reaction complexes are observed to identify the addition of specific nucleotides in a template dependent fashion, and thus derive the sequence of that template.

In particular, nucleic acid synthesis complexes that typically comprise a nucleic acid polymerase, a template sequence and a primer sequence are provided immobilized upon the surface of a substrate. Such complexes may be immobilized through a coupling of the polymerase to the surface or through coupling of the template and or the primer sequence. Such coupling may be covalent, or may include any of a variety of noncovalent linkages, e.g., hybridization, biotin-streptavidin linkages, or the like.

The overall substrate upon which the complexes are immobilized, is imaged upon a sensor array during the primer extension reaction, and the position of fluorescent signals associated the complex's reaction with a fluorescently labeled nucleotide is detected upon the sensor. In accordance with the invention, the centroid, or in some cases, centroids for a given signal, is determined. Where two complexes are in sufficient proximity, differing centroids for signal events will provide a basis for distinction of these signals. This will occur regardless of whether those signals are concurrent or temporally discrete. In particular, if a given signal at a given time includes distinct centroids (showing two or more centroids), then it can be identified as arising from more than one complex. Where signals are temporally discrete, the determination of a centroid will allow assignment of each signal to a discrete, although not otherwise optically resolvable complex.

Figure 3A:
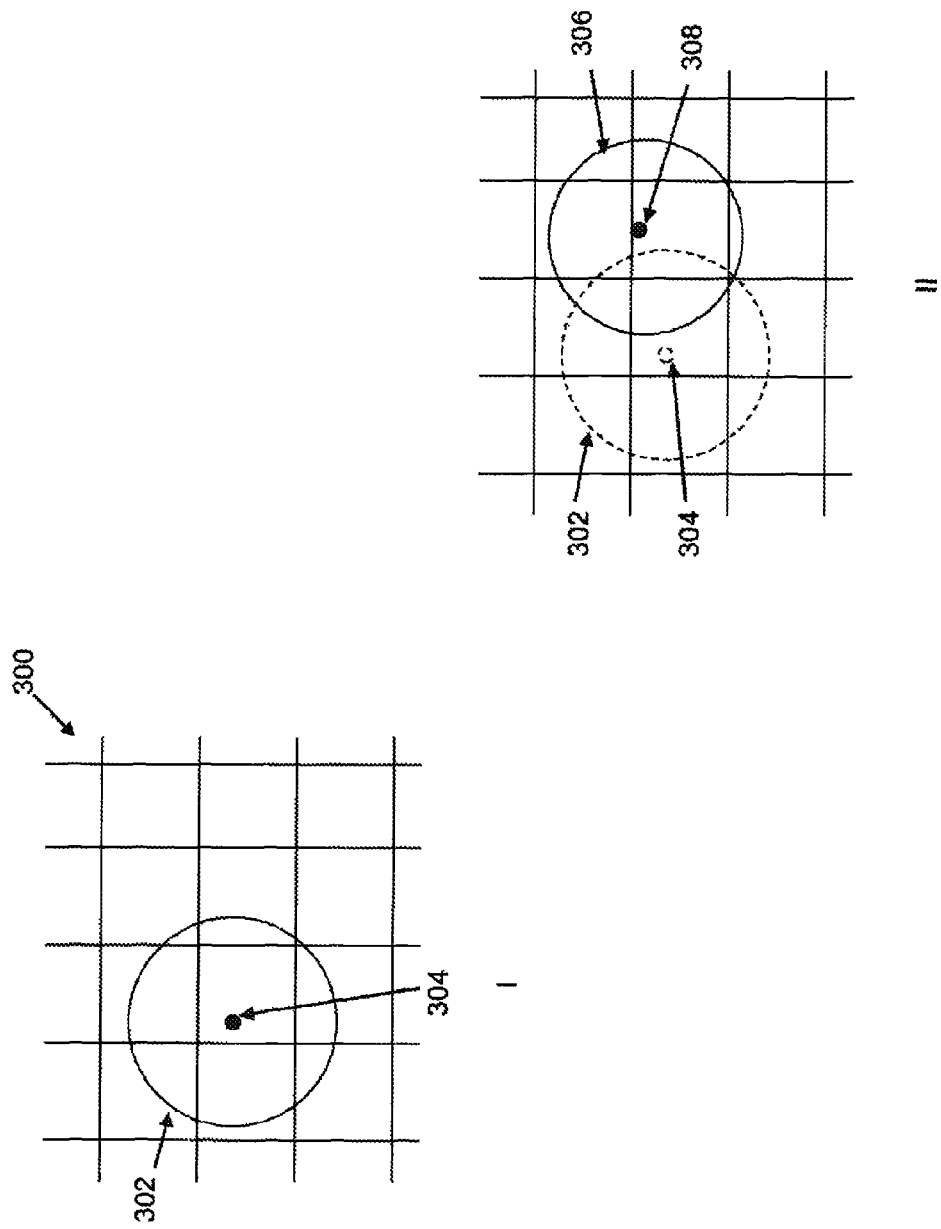
FIGS. 3a and 3b illustrate centroid location within overlapping and non-overlapping signal images and application of such centroids in subsequent data analysis.
Figure 3B:
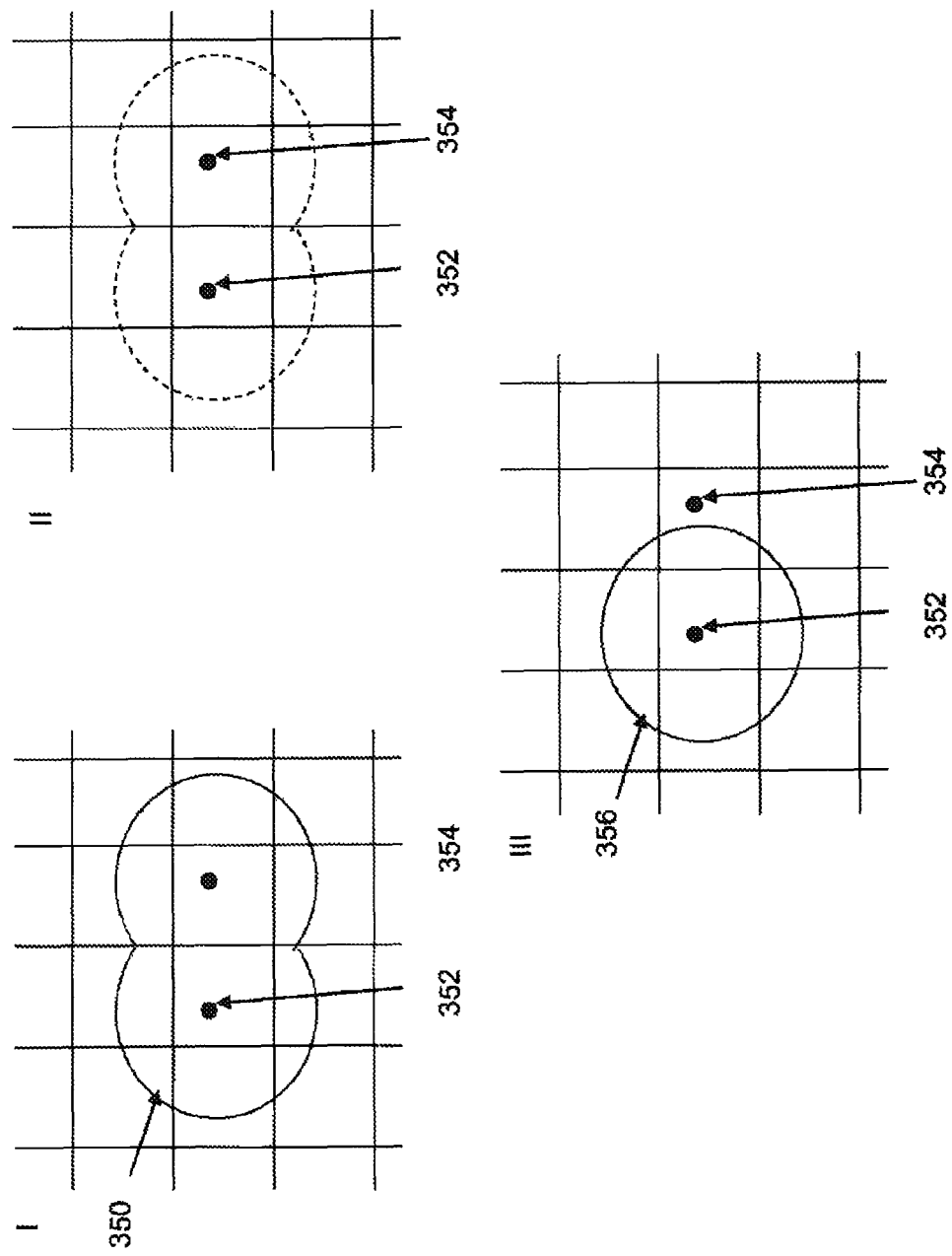

Both of the foregoing exemplary scenarios are schematically illustrated in FIGS. 3A and 3B. FIG. 3A schematically illustrates two signal events imaged on a detector array 300 that are temporally discrete but positionally overlap (i.e., they overlap in position by some fraction), a first signal event is imaged on a portion of a sensor array 300 (shown in close up as signal image 302). A centroid 304 is identified for that first signal image 302. A subsequent or second signal event is imaged upon a portion of the sensor array in a second signal image 306. As shown, the second signal image 306 substantially overlaps with the location upon which the first signal event was imaged (as shown by the dashed circle representing first signal image 302). Again, a centroid 308 is determined for the second signal image 306.

These positionally overlapping signal images (signal images 302 and 306) could potentially lead to confused signals/data, as they result from different reaction complexes, but are not positionally distinguishable. As a result, consideration of these signals could lead to erroneous data in which a particular signal is attributed to a different reaction center or complex, e.g., in nucleic acid sequencing, as a called base for a first template directed synthesis reaction may actually have emanated from a different template mediated process.

In accordance with the present invention, however, while the first and second signal images substantially overlap in terms of the location upon the sensor at which they were imaged, they may nonetheless be characterized as emanating from discrete reaction complexes, as they have positionally discrete centroids (304 and 308). As a result of the assignment of different signal components as arising from different reaction centers, the data from each signal component can be separately recorded, and analyzed.

Alternatively, where two reaction centers produce signals that overlap both spatially and temporally, e.g., as illustrated in FIG. 2, the processes of the invention can be utilized to identify such overlapping reaction centers in order to either distinguish data from each of the reaction centers, or preferably, annotate all such signals emanating from this signal location as being subjected to an overlapping reaction center signal. In particular, as shown in FIG. 3B, panel I, a signal that results from spatially and temporally overlapping reaction centers is imaged on a sensor to yield image 350. As shown in panel II, multiple centroids, e.g., centroid 352 and 354, are identified for the single signal image 350. Because multiple centroids are identified, one can identify this signal as emanating from multiple reaction centers and thus treat such signals or future signals from the same location, as being subject to this issue. In particular, one may elect to ignore all such signals from this location, or in some cases, assign a confidence weighting to such signals that can instruct subsequent data analysis, e.g., in providing quality scores for the data obtained.

In still other alternatives, the determined centroids can be used for interpretation of subsequent data that corresponds to only one of the centroids, e.g., for subsequent signals that do not have a temporally overlapping signal component from the adjacent reaction center. By way of example, as shown in FIG. 3B, panel III, a subsequent signal image 356 yields a single centroid that corresponds to only one of centroids 352 and 354 (shown in panel II, as open circles). As a result, it can be interpreted as a single isolated signal emanating form the reaction complex that yielded the single signal centroid, e.g., centroid 352 as shown, and the data derived therefrom can be interpreted accordingly.

IV. Additional Positional Applications

In addition to the application of positional information to the deconvolution of overlapping signal images, one may also employ such positional elucidation to identify relative positions of different contributors to a signal event, e.g., to identify the orientation and/or position of one or more members of a complex on a substrate. In particular, in analyzing the interaction of an immobilized reactant, e.g., an enzyme such as a DNA polymerase, and a substrate, e.g., a nucleotide, or primer template complex, one can provide each component with a distinguishable and detectable label group such as a fluorescent dye group. Upon interaction between the two components, an overlapping signal image of the distinguishable signals will be generated. Because these signals are distinguishable, e.g., having differing spectral characteristics, they are readily discernible. However, by identifying the position of each signal relative to the other during their interaction, one can ascertain their relative orientation. For example, signals that are directly interposed may be indicative that the active site of the enzyme (or other interactive component of another type of reactant) is directly vertically oriented, while signals that appear displaced slightly may indicate an orientation where an enzyme is on its side on the substrate. Of course, specific orientation data may be calibrated in accordance with orientations that produce optimal results for a given application. For example, in some cases, it may be desirable from a functional standpoint, for an enzyme to be oriented on its side, rather than vertically relative to the surface of a substrate. In a related aspect, positional information for a first reactant and a second reactant may readily identify when an interaction is specific, e.g., reacting at an active site, vs. non-specific, e.g., binding to a portion of the enzyme that is not the active site or binding somewhere on the substrate near the enzyme. As will be appreciated, other methods may be used to distinguish the label of a fixed component versus a freely diffusing component. For example, one may employ polarized excitation illumination and polarized detection optics. The emitted signals from the immobilized component would be expected to be detected without substantial depolarization, while the freely diffusing labeled components would return substantially more depolarized signals (for a discussion of the detection of polarized and depolarized components from relatively fixed and relatively freely diffusing components, see, e.g., U.S. Pat. No. 7,122,659).

As will be appreciated, any of a variety of different labeling techniques may be employed to distinguish the signal contributions of different reactants, including, e.g., spectrally distinguishable fluorescent dyes or particles, such as quantum dots, labels having different de-polarizing properties, or the like.

V. Exemplary Processes

The processes of the present invention find utility in a wide variety of analytical applications, where one desires to distinguish two closely spaced signal producing regions, e.g., reaction centers.

A. Single Molecule Real Time Nucleic Acid Sequencing

In one exemplary application, as alluded to above, individual molecular complexes are monitored in real time to observe the reaction as it occurs on a single molecule, or at least single complex basis. One illustrative example is the monitoring of individual DNA polymerase complexes as they are involved in the replication of DNA. In particular, by observing the action of a single DNA polymerase as it engages in template directed DNA replication, one can elucidate the underlying sequence of the DNA template by identifying the addition of complementary bases, in real time. This is typically carried out by providing labeled nucleotides to the polymerase and detecting them as they are incorporated into the synthesized DNA strand, using a process that allows discrimination between the added labeled nucleotide and those labeled nucleotides that are in the solution, but not being incorporated. Such methods include providing the synthesis complex immobilized within an optically confined region, such that only the reaction complex is illuminated, and only incorporating nucleotides are seen for sufficient time to indicate incorporation (See, e.g., Eid, et al., *Science* (2009): Vol. 323. no. 5910, pp. 133-138, and U.S. Pat. No. 7,485,424). Alternatively, cooperative label methods may be used whereby a donor fluorophore is provided associated with the polymerase enzyme, while acceptor fluorophores are provided on the nucleotides. When these cooperative labels, e.g., FRET pairs, are brought into sufficient proximity during an incorporation event, a characteristic energy transfer signal is created and detected (See, e.g., U.S. Pat. No. 7,416,844).

The methods of the invention are used to determine whether a given signal event is deriving from a single reaction center or multiple reaction centers, and, in some cases, deconvolve overlapping signals. In particular, by identifying signal events that include more than one centroid, one can determine that such signals likely emanate from more than one reaction center. Where signals are identified as potentially coming from more than a single reaction center, it can be discarded as less useful, given that it represents confounding signals. Alternatively, by identifying two distinct, although not optically resolvable reaction centers, one may further process the signal data to derive useful single complex data. For example, one may be able to sufficiently distinguish signals from each center, whether they are temporally distinct or not, such that one can attribute such signals to the different centers.

B. Reaction Localization in High Density Arrays

Other analytical configurations are also amenable to the methods of the invention, where one is desirous of analyzing reaction centers at high densities, whether at the single molecule level or as ensembles of molecules, e.g., in spots or patches, on a substrate surface. By way of example, in a number of analytical operations, groups or patches of molecules are deposited on a surface in either a random or arrayed or gridded format of reaction zones. These arrays of reaction zones are then observed following exposure to different reaction conditions, e.g., exposure to drug candidates, nucleic acid probes, binding molecules, or the like. In a simple example, arrays of immobilized nucleic acids are probed with labeled nucleic acid probes to identify complementary sequences to those probes. Other applications include ensemble based sequencing by synthesis reactions, protein arrays, and others.

In such applications, in order to increase the throughput or multiplex of a given analysis, one must increase the number of reaction centers per unit area. As will be appreciated, this approach has been limited by the ability to optically resolve adjacent reaction centers. In accordance with the invention, however, one can closely pack reaction centers together, and resolve them using the centroid approach set forth herein. In particular, in setting up reaction centers, many applications utilize inter-zone or feature spacing on the order of microns. This can dramatically reduce the overall available density, particularly where each feature may be an order of magnitude smaller than such spacing. In accordance with the invention, however, feature size and feature spacing may each be on the smaller scale, allowing much higher densities of reaction zones per unit area on an array, e.g., 1 micron features with 1 micron spacing, or even less, e.g., 0.1 micron, 0.01 micron, or the like.

C. Signal to Noise Ratio Enhancement

In still another application, the attribution of signal events to a fixed or pre-identified reaction center centroid also allows one the ability to distinguish true reaction signals from other errant signal events that may occur sufficiently proximal to the reaction center as to give a confounding background signal. Such errant signal events include non-specific interactions between label reagents and molecular complexes or the substrate, background diffusion of signal producing reagents, and the like. Where such signals occur, they are substantially distinguishable from the reactions occurring at the reaction center, as they will not share the same signal centroid. Accordingly, by filtering out non-centroid deriving signal events, one can produce a signal event with a higher signal to noise ratio.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A method of monitoring single molecule reactions at a first and a second single molecule reaction complex, comprising:

providing a first single molecule reaction complex and a second single molecule reaction complex, each at least partially immobilized on a substrate, exposing the first and second single molecule reaction complexes to reaction conditions;

wherein said first single molecule reaction complex produces a first optically detectable signal indicative of the presence of a single molecule reaction at the first single molecule reaction complex and the second single molecule reaction complex produces a second optically detectable signal indicative of the presence of a single molecule reaction at the second single molecule reaction complex, wherein the first and second optically detectable signals are not completely optically resolvable from each other;

positionally detecting the first optically detectable signal and the second optically detectable signal;

identifying a first positional centroid for the first optically detectable signal and a second positional centroid for the second optically detectable signal; and characterizing the first optically detectable signal as emanating from the first single molecule reaction complex based upon the first positional centroid and characterizing the second optically detectable signal as emanating from the second single molecule reaction complex based upon the second positional centroid, and;

detecting a plurality of optically detectable signals from the first and second single molecule reaction complexes and assigning each of said plurality of signals as emanating from either the first or second single molecule reaction, complex based upon a comparison of a positional centroid of each of the plurality of optically detectable signals with a positional centroid determined from the first and second single molecule reaction complexes.

2. The method of claim 1, wherein the identification of the first positional centroid is determined at the sub-pixel level.

3. The method of claim 1, wherein the first single molecule reaction complex comprises a nucleic acid polymerase/template/primer complex.

4. The method of claim 3, wherein the first optically detectable signal indicative of the presence of the first single molecule reaction complex comprises a fluorescent signal indicative of polymerase mediated extension of a primer in the complex to produce an extended primer.

5. The method of claim 4, wherein the first optically detectable signal comprises a fluorescent label on a labeled nucleotide or nucleotide analog that has been incorporated into or is being incorporated into the extended primer.

6. The method of claim 5, wherein the labeled nucleotide is labeled upon a portion of the nucleotide that is retained upon the nucleotide following incorporation.

7. The method of claim 5, wherein the labeled nucleotide is labeled upon a portion of the nucleotide that is not retained upon the nucleotide following incorporation.

8. The method of claim 1, wherein the first and second optically detectable signals comprise substantially the same spectrum.

9. The method of claim 1, wherein the first and second optically detectable signals comprise different spectra.

10. The method of claim 1, wherein the first single molecule reaction complex comprises a nucleic acid polymerase/template/primer complex, and the first optically detectable signal comprises a fluorescent signal emanating from a nucleotide that has been or is being incorporated into a primer extension reaction by the polymerase, the optically detectable signal being indicative of a type of nucleotide that is incorporated or being incorporated.

11. The method of claim 1, wherein the first and second optically detectable signals are temporally distinct.

* * * * *